(12) United States Patent
Schlueter

(10) Patent No.: US 7,119,210 B2
(45) Date of Patent: Oct. 10, 2006

(54) DUAL FUNCTION UV-ABSORBERS FOR OPHTHALMIC LENS MATERIALS

(75) Inventor: Douglas C. Schlueter, Azle, TX (US)

(73) Assignee: Alcon, Inc., Hunenberg (CH)

( * ) Notice: Subject to any disclaimer, the term of this patent is extended or adjusted under 35 U.S.C. 154(b) by 303 days.

(21) Appl. No.: 10/753,254

(22) Filed: Jan. 8, 2004

(65) Prior Publication Data

US 2004/0157948 A1 Aug. 12, 2004

Related U.S. Application Data

(60) Provisional application No. 60/438,978, filed on Jan. 9, 2003.

(51) Int. Cl.
C07D 249/16 (2006.01)

(52) U.S. Cl. .................. 548/260; 548/257; 526/313

(58) Field of Classification Search ............... 526/313; 548/257, 260
See application file for complete search history.

(56) References Cited

U.S. PATENT DOCUMENTS

| | | | | |
|---|---|---|---|---|
| 3,956,269 A | * | 5/1976 | Sheppard et al. | 534/886 |
| 4,304,895 A | * | 12/1981 | Loshaek | 526/313 |
| 4,528,311 A | | 7/1985 | Beard et al. | 524/91 |
| 4,612,358 A | | 9/1986 | Besecke et al. | 526/259 |
| 4,716,234 A | | 12/1987 | Dunks et al. | 548/259 |
| 4,785,063 A | | 11/1988 | Slongo et al. | 548/259 |
| 4,929,250 A | | 5/1990 | Hung et al. | 8/507 |
| 4,963,160 A | | 10/1990 | Hung et al. | 8/507 |
| 5,098,445 A | | 3/1992 | Hung et al. | 8/507 |
| 5,133,745 A | | 7/1992 | Falcetta et al. | 623/6 |
| 5,141,990 A | | 8/1992 | McKoy et al. | 522/4 |
| 5,147,902 A | | 9/1992 | Ichikawa et al. | 523/106 |
| 5,164,462 A | | 11/1992 | Yang | 525/478 |
| 5,189,084 A | | 2/1993 | Birbaum et al. | 524/100 |
| 5,194,544 A | | 3/1993 | Goldberg et al. | 526/259 |
| 5,290,892 A | | 3/1994 | Namdaran et al. | 526/259 |
| 5,298,033 A | | 3/1994 | Hung et al. | 8/509 |
| 5,331,073 A | | 7/1994 | Weinschenk, III et al. | 526/264 |
| 5,384,235 A | | 1/1995 | Chen et al. | 430/512 |
| 5,399,692 A | | 3/1995 | Hung et al. | 544/327 |
| 5,500,024 A | | 3/1996 | Hung et al. | 8/509 |
| 5,648,488 A | | 7/1997 | Stevenson | 544/215 |
| 5,693,095 A | | 12/1997 | Freeman et al. | 623/6 |
| 5,837,792 A | | 11/1998 | Meuwly et al. | 528/27 |
| 5,869,588 A | | 2/1999 | Toan et al. | 526/261 |
| 5,914,355 A | | 6/1999 | Künzler | 523/106 |
| 5,928,629 A | | 7/1999 | Allard et al. | 424/59 |
| 5,928,630 A | | 7/1999 | Richard et al. | 424/59 |
| 5,942,564 A | | 8/1999 | Kaschig et al. | 524/100 |
| 5,945,465 A | | 8/1999 | Ozark et al. | 523/106 |

FOREIGN PATENT DOCUMENTS

| | | |
|---|---|---|
| EP | 0 221 630 A2 | 7/1986 |
| EP | 0 343 996 A2 | 5/1989 |
| EP | 0 283 166 B1 | 1/1992 |
| EP | 0 693 483 A1 | 1/1996 |
| EP | 0 952 467 A1 | 10/1999 |
| EP | 0 582 664 B1 | 10/2000 |
| WO | WO 98/50371 | 11/1998 |
| WO | WO 00/55212 | 9/1999 |
| WO | WO 99/53348 | 10/1999 |
| WO | WO 99/58507 | 11/1999 |
| WO | WO 99/60428 | 11/1999 |
| WO | WO 99/63366 | 12/1999 |
| WO | WO 02/078966 | 10/2002 |

OTHER PUBLICATIONS

Dickstein et al., "Functional Polymers. XXVI. Co– and Terpolymers Involving Methacrylates, N–Vinylpyrollidone, and Polymerizable Ultraviolet Stabilizers and Antioxidants," *J. Macromol. Sci–Chem.* A22(4), pp. 387–402 (1985).

DeGroot et al., "Hydrophilic Polymeric Acylphospine Oxide Photoinitiators/Crosslinkers for in Vivo Blue–Light Photopolymerization," *Biomacromolecules*, vol. 2, pp. 1271–1278 (2001).

Keck et al., Deactivation Processes of 2–Hydroxyphenyl–1, 3,5–Triazines–Polymeric and Monomeric UV Absorbers of the Benzotriazole and Triazine Class, *Die Angewandte Makromolekulare Chemie*, vol. 252, pp. 119–138 (1997).

Knaus et al., "Photoinitiators with Functional Groups. III. Water–Soluble Photoinitiators Containing Carbohydrate Residues," *J. of Polymer Science*, vol. 33, pp. 929–939 (1995).

Pan et al., "Synthesis and Characterization of New Monomers Containing UV–absorber Function," *Polymer Degradation and Stability*, vol. 49, pp. 231–237 (1995).

Rabek, J.F. *Photostabilization of Polymers*, Elsevier Applied Science, London and New York (1990), Chapter 1.1–1.3 (pp. 1–5); Chapter 5.1–5.10 (pp. 202–249); and Chapter 7.3 (pp. 368–391).

Sustic et al., "New 2(20hydroxyphenyl)2H–benzotriazole based polymer–bound ultraviolet stabilizers," *ACS Polymer Prep.* vol. 28(2), p. 226 (1987).

\* cited by examiner

*Primary Examiner*—Paul J. Killos
(74) *Attorney, Agent, or Firm*—Patrick M. Ryan

(57) ABSTRACT

Disclosed are UV absorbers that contain a labile functional group capable of initiating free radical polymerization.

4 Claims, No Drawings

DUAL FUNCTION UV-ABSORBERS FOR OPHTHALMIC LENS MATERIALS

This application claims priority to U.S. Provisional Application, U.S. Ser. No. 60/438,978, filed Jan. 9, 2003.

FIELD OF THE INVENTION

This invention is directed to ophthalmic lens materials. In particular, this invention relates to ultraviolet light absorbers that also act as polymerization initiators for ophthalmic lens materials.

BACKGROUND OF THE INVENTION

Many UV light absorbers are known as ingredients for polymeric materials used to make ophthalmic lenses. UV absorbers are preferably covalently bound to the polymeric network of the lens material instead of simply physically entrapped in the material to prevent the absorber from migrating, phase separating or leaching out of the lens material. Such stability is particularly important for implantable ophthalmic lenses where the leaching of the UV absorber may present both toxicological issues and lead to the loss of UV blocking activity in the implant.

Numerous copolymerizable benzatriazole, benzophenone and triazine UV absorbers are known. Many of these UV absorbers contain conventional olefinic polymerizable groups, such as methacrylate, acrylate, methacrylamide, acrylamide or styrene groups. Copolymerization with other ingredients in the lens materials, typically with a radical initiator, incorporates the UV absorbers into the resulting polymer chain. Incorporation of additional functional groups, on a UV absorber may influence one or more of the UV absorber's UV absorbing properties, solubility or reactivity. If the UV absorber does not have sufficient solubility in the remainder of the ophthalmic lens material ingredients or polymeric lens material, the UV absorber may coalesce into domains that could interact with light and result in decreased optical clarity of the lens.

Examples of polymeric ophthalmic lens materials that incorporate UV absorbers can be found in U.S. Pat. Nos. 5,290,892; 5,331,073 and 5,693,095.

SUMMARY OF THE INVENTION

The present invention provides dual function UV absorbers. These UV absorbers contain a labile functional group capable of initiating radical polymerization. These UV absorbers are suitable for use in ophthalmic lenses, including contact lenses, and are particularly useful in implantable lenses, such as intraocular lenses (IOLs).

Among other factors, the present invention is based on the finding that UV absorbers can be modified to incorporate a labile functional group capable of initiating polymerization of an olefinic ophthalmic lens material monomers without eliminating the UV absorber's UV absorbing activity, solubility or reactivity with ophthalmic lens material ingredients.

DETAILED DESCRIPTION OF THE INVENTION

Unless indicated otherwise, all ingredient amounts expressed in percentage terms are presented as % w/w.

The dual function UV absorbers ("DFUVAS") of the present invention contain a functional group that can initiate free radical polymerization. As such, these DFUVAS eliminate the need for two separate monomeric ingredients in the preparation of copolymeric ophthalmic lens materials. Instead of adding a conventional UV absorber to conventional ophthalmic lens-forming materials and separately adding a conventional polymerization initiator, a DFUVAS can be used in place these two conventional ingredients.

Many conventional thermal free radical initiators and many UV absorbers are known. The DFUVAS may be synthesized by reacting a UV absorber that contains a reactive functionality with a radical initiator while preserving the radical generating linkage. For example, 3-(2H-benzotriazol-2-yl)-4-hydroxyphenethyl alcohol (1) may be coupled to 4,4'-azobis(4-cyanopentanoic acid) (2) using a carbodiimide esterification agent. The product (3) can then initiate radical polymerization of a vinyl monomer (e.g., acrylate, methacrylate, acrylamide, methacrylamide, styrene) by application of heat and/or UV/visible light and the UV absorbing functionality will be covalently attached to the polymer chain.

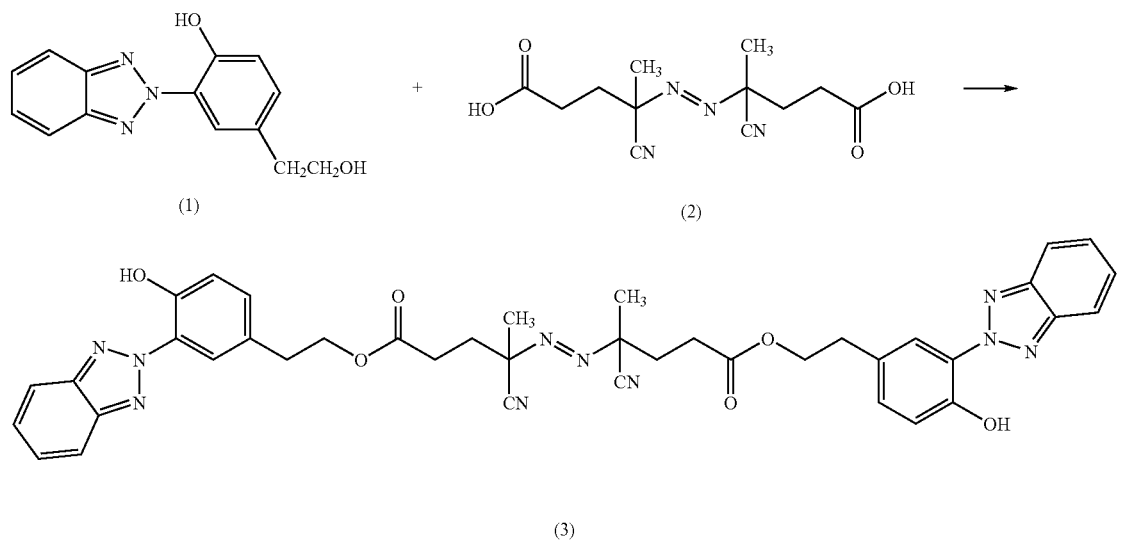

This invention provides the synthesis of a single component additive that provides a dual function: UV absorption properties and ability to initiate free radical polymerization. The result is a covalently linked UV absorber that will not leach out of the product or phase separate and lead to decreased optical clarity. The synthesis permits flexibility in tailoring both UV absorbing strength and initiator half-life. UV-initiation of polymerization of the lens material is still possible with protection of the hydroxy group on the UV absorbing function of the DFUVAS.

The DFUVAS can be synthesized from azo, organic peroxide, phosphine oxide, and α-hydroxyketone radical polymerization initiators that contain appropriate functional groups. The necessary functionality from each of these initiator classes is the presence of a functional group (carboxylic acid or hydroxyl) through which a UV absorbing benzotriazole, benzophenone or triazine can be covalently linked. Preferred DFUVAS are those represented by formulas [1]–[7].

Several functionalized azo initiators are commercially available. For example, V-501 (4,4'-azobis(4-cyanopentanoic acid)) from Wako Chemicals. This initiator contains a thermally labile azo linkage (—N=N—) and two terminal carboxylic acid groups. Similarly, VA-086 contains two terminal hydroxyl groups. VA-080 contains three hydroxyl groups on each side of the thermally labile azo linkage.

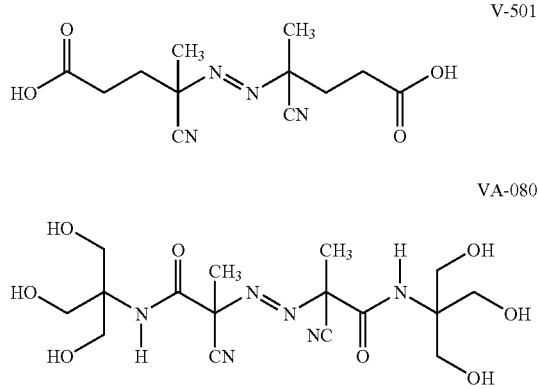

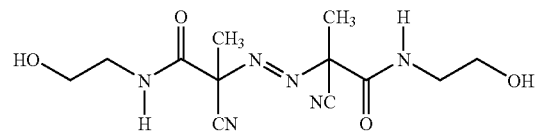

Therefore, an azo functional UV absorber can be synthesized from an azo initiator with the following structural characteristics:

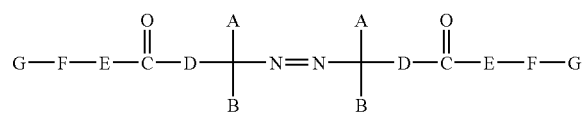

where:
A is —CH$_3$ or —CH$_2$CH$_3$.
B is —CN, —CO$_2$H, —COH, —COCH$_3$, —CO$_2$CH$_3$, —SO$_3$H, —CF$_3$, or —NO$_2$ when (CH$_2$)$_n$, and —CH$_3$ or —CH$_2$CH$_3$ when D is nothing.
D is nothing or (CH$_2$)$_n$, n=1–10
E is O or NH, NCH$_3$, or NCH$_2$CH$_3$
F is nothing, (CH$_2$)$_x$, or (CH$_2$CH$_2$O)$_x$CH$_2$CH$_2$ where x=1–10.
G is —R, —OR, —NHR', —NRR', —CO$_2$R, or —COR, where R=a benzotriazole or benzophenone UV absorber, and R'=—CH$_3$ or —CH$_2$CH$_3$.

Many benzotriazole and benzophenone UV absorbers are known and many are commercially available from a variety of sources, such as Ciba Specialty Chemicals. The identity of the benzotriazole or benzophenone UV absorber is not critical, but should be selected based on its characteristic UV cut-off to give the desired UV absorbing property. For IOL applications, preferred benzotriazole UV absorbers are hydroxyphenylbenzotriazoles and preferred benzophenone UV absorbers are hydroxyphenylbenzophenones that have been modified to contain a functional group that can be covalently bonded to a radical polymerization initiator. For example, a preferred hydroxyphenylbenzotriazole UV absorber is 2-N-(2-hydroxyphenyl)benzotriazole, where the UV absorbing group is linked through an ethyl ether linkage at the para position on the hydroxyphenyl group, as shown below linked to an azo functionality.

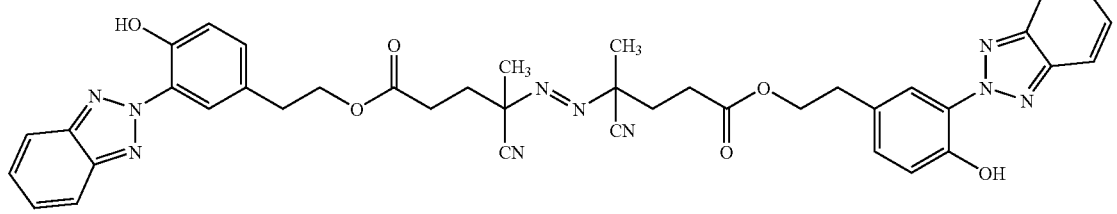

Functionalized α-hydroxyketones suitable for use as UV polymerization initiators are commercially available. For example, 2-hydroxy-1-[4-(2-hydroxy-ethoxy)phenyl]-2-methylpropan-1-one (Irgacure® 2959, Ciba Specialty Chemicals) contains a free primary hydroxyl group covalently attached to a UV light labile α-hydroxyketone linkage. This primary hydroxyl can be used as a covalent linking point. For example, in Irgacure® 2959, the primary hydroxyl was used to covalently attach hydrophilic functional groups through an ether linkage to create a water-soluble photoinitiator (Gruber, H. F.; Knaus, S. J. Polym. Sci. Part A: Polym. Chem. 1995, 33, 929).

Irgacure® 2959

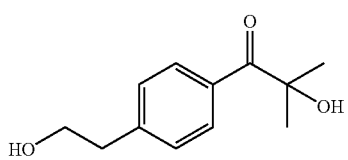

A generic α-hydroxyketone photoinitiator that contains the appropriate functional groups for covalently linking a UV chromophore is represented by formula [2]:

[2]

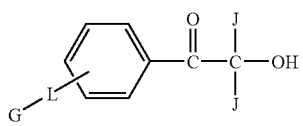

where:
J is $CH_3$ or $CH_2CH_3$.
L is nothing, $(CH_2)_y$, or $(CH_2CH_2O)_y$ where y=1–10.
G is —R, —OR, —NHR, —NRR', —$CO_2$R, or —COR, where R=a benzotriazole or benzophenone UV absorber, and R'=—$CH_3$ or —$CH_2CH_3$.

Functionalized phosphine oxide photoinitiators are also known. For example, a vinyl functional phosphine oxide was used in the synthesis of polymeric acylphosphine oxide photoinitiators (DeGroot, J. H.; Dillingham, K. A.; Deuring, H.; Haitjema, H. J.; Van Beijma, F. J.; Hodd, K. A.; Norrby, S. *Biomacromolecules* 2001, 2, 1271).

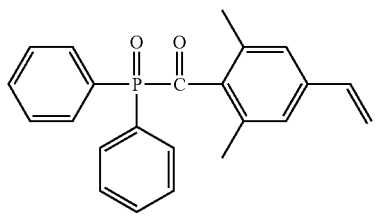

A generic phosphine oxide photoinitiator that contains the appropriate functional groups for covalently linking a UV chromophore is represented by formula [3].

[3]

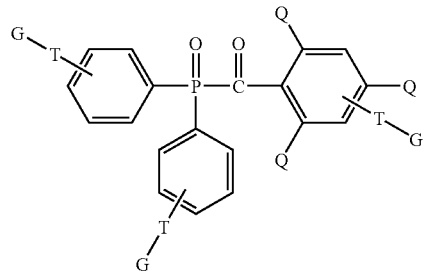

where Q is —H, —$CH_3$, —$CH_2CH_3$, —$CH(CH_3)CH_3$, or —$C(CH_3)_3$.

T is nothing, —$(CH_2)_z$, or —$(OCH_2CH_2)_z$, where z=1–10
G is —R, —OR, —NHR, —NRR', —$CO_2$R, or —COR, where R=a benzotriazole or benzophenone UV absorber, and R'=—$CH_3$ or —$CH_2CH_3$.

Functionalized organic peroxides are less common, however the presence of a functional group for example OH, $NH_2$, or $CO_2H$ would allow covalent attachment of a benzotriazole- or benzophenone-containing UV chromophore. A generic acylperoxide initiator that contains appropriate functional groups for covalently linking a UV chromophore is represented by formula [4].

[4]

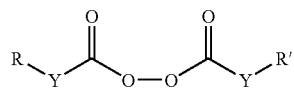

where Y=nothing or O; R=a benzotriazole or benzophenone UV absorber; R'=a benzotriazole or benzophenone UV absorber; —$(CH_2)_n$H (n=1–18); —$CH(CH_3)$ $CH_3$; —$C(CH_3)_3$; —$C_6H_5$; —$CH(CH_3)CH_2CH_3$; —$C(CH_3)_2$ $CH_2C(CH_3)_3$; —$C(CH_3)_2(CH_2)_4$H; —$C(CH_2CH_3)_2(CH_2)_4$ H; —$C(CH_3)_2(CH_2)_5$H; —$C(CH_2CH_3)_2$ $(CH_2)_5$H; —$C(CH_3)_2(CH_2)_6$H; —$C(CH_2CH_3)_2(CH_2)_6$H; —$CH_2CH(CH_2CH_3)(CH_2)_4$H; or

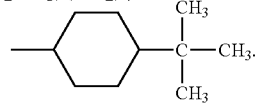

By way of illustration, if Y=O and R and R' in formula [4] are selected to be the benzotriazole UV absorber 2-N-(2-hydroxyphenyl)benzotriazole, and the UV absorbing group is linked through an ethyl linkage at the para position on the hydroxyphenyl group to the peroxydicarbonate functionality, the following compound is obtained:

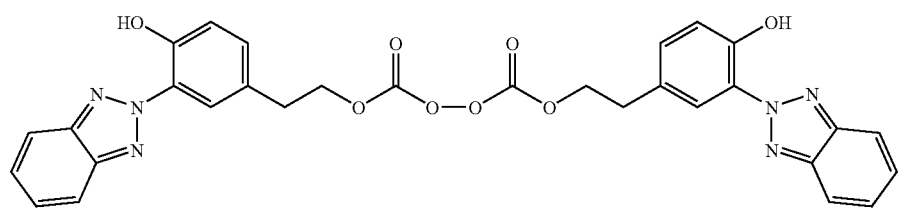

Generic peroxyester, dialkylperoxide and peroxyketal initiators that contain the appropriate functional groups for covalently linking a UV chromophore are represented by formulas [5], [6], and [7], respectively.

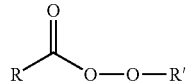

(peroxyester)
where R=a benzotriazole or benzophenone UV absorber; R'=a benzotriazole or benzophenone UV absorber; —(CH$_2$)$_n$H (n=1–18); —CH(CH$_3$)CH$_3$; —C(CH$_3$)$_3$; —C$_6$H$_5$; —CH(CH$_3$)CH$_2$CH$_3$; —C(CH$_3$)$_2$CH$_2$C(CH$_3$)$_3$; —C(CH$_3$)$_2$(CH$_2$)$_4$H; —C(CH$_2$CH$_3$)$_2$(CH$_2$)$_4$H; —C(CH$_3$)$_2$(CH$_2$)$_5$H; —C(CH$_2$CH$_3$)$_2$(CH$_2$)$_5$H; —C(CH$_3$)$_2$(CH$_2$)$_6$H; —C(CH$_2$CH$_3$)$_2$(CH$_2$)$_6$H; —CH$_2$CH(CH$_2$CH$_3$)(CH$_2$)$_4$H; —C(CH$_3$)$_2$C$_6$H$_5$; or

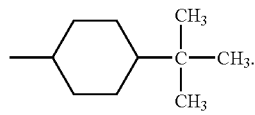

R—O—O—R (dialkylperoxide) [6]

where R=a benzotriazole or benzophenone UV absorber; R'=H, a benzotriazole or benzophenone UV absorber; —(CH$_2$)$_n$H (n=1–18); —CH(CH$_3$)CH$_3$; —C(CH$_3$)$_3$; —CH(CH$_3$)CH$_2$CH$_3$; —C(CH$_3$)$_2$CH$_2$C(CH$_3$)$_3$; —C(CH$_3$)$_2$(CH$_2$)$_4$H; —C(CH$_2$CH$_3$)$_2$(CH$_2$)$_4$H; —C(CH$_3$)$_2$(CH$_2$)$_5$H; —C(CH$_2$CH$_3$)$_2$(CH$_2$)$_5$H; —C(CH$_3$)$_2$(CH$_2$)$_6$H; —C(CH$_2$CH$_3$)$_2$(CH$_2$)$_6$H; —CH$_2$CH(CH$_2$CH$_3$)(CH$_2$)$_4$H; or —C(CH$_3$)$_2$C$_6$H$_5$.

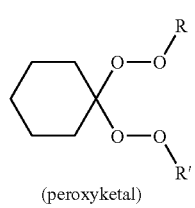

(peroxyketal)

where R=a benzotriazole or benzophenone UV absorber;
R'=H; a benzotriazole or benzophenone UV absorber; (CH$_2$)$_n$H (n=1–18); CH(CH$_3$)CH$_3$; C(CH$_3$)$_3$; CH(CH$_3$)CH$_2$CH$_3$; C(CH$_3$)$_2$C(CH$_3$)$_3$; C(CH$_3$)$_2$(CH$_2$)$_4$H; C(CH$_2$CH$_3$)$_2$(CH$_2$)$_4$H; C(CH$_3$)$_2$(CH$_2$)$_5$H; C(CH$_2$CH$_3$)$_2$(CH$_2$)$_5$H; C(CH$_3$)$_2$(CH$_2$)$_6$H; C(CH$_2$CH$_3$)$_2$(CH$_2$)$_6$H; CH$_2$CH(CH$_2$CH$_3$)(CH$_2$)$_4$H; or C(CH$_3$)$_2$C$_6$H$_5$.

In general, the amount of DFUVAS contained in ophthalmic lens materials will depend upon the desired UV blocking characteristics but will typically range from 1–5 wt %.

The invention will be further illustrated by the following examples, which are intended to be illustrative, but not limiting.

Example 1

Esterification of 4,4'-azobis(4-cyanopentanoic acid) with 3-(2H-benzotriazol-2-yl)-4-hydroxyphenethy alcohol A 50 mL 3-neck flask was dried in a 120° C. oven overnight and cooled in a desiccator. The flask flushed with N$_2$ then charged with 1.9151 g (7.50 mmol) of 3-(2H-benzotriazol-2-yl)4-hydroxyphenethyl alcohol. The solid was dissolved in 15 mL anhydrous tetrahydrofuran, then 4-dimethylaminopyridine (0.0489 g, 0.400 mmol) and 4,4'-azobis(4-cyanopentanoic acid) (1.0084 g, 3.60 mmol), were added and allowed to dissolve. 1,3-Dicyclohexyl carbodiimide (1.5520 g, 7.52 mmol) was added and the reaction mixture was allowed to stir at ambient temperature under a N$_2$ blanket for 24 hr. The reaction mixture was filtered through a fine porosity sintered glass funnel and the solvent was rotovapped. The crude product was purified by column chromatography (silica gel, CH$_2$Cl$_2$), the solvent was rotovapped and the product was dried under vacuum. Yield 1.3691 g (1.81 mmol, 51%) of a pale yellow powder.

Example 2

Preparation of Ophthalmic Lens Material initiated with UV absorbing inititator prepared in Example 1.

A scintillation vial was charged with 3.3572 g (19.052 mmol) of 2-phenylethyl acrylate (PEA), 1.5585 g (8.192 mmol) of 2-phenylethyl methacrylate (PEMA), and 0.0611 g (0.308 mmol) of 1,4-butanediol diacrylate (BDDA). The monomer mixture was purged with N$_2$ and 0.2290 g (0.304 mmol) of the UV absorbing initiator prepared in Example 1 was added and allowed to dissolve. The initiated formulation was filtered through a 0.2 micron PTFE filter and dispensed into polypropylene molds. The molds were placed in an oven for 1 hr at 70° C. then 2 hrs at 110° C. The product polymer was extracted in acetone at room temperature for 16 hrs. The polymer was allowed to air dry for 1.5 hr, then placed in a 60° C. vacuum oven for 3 hrs. The weight loss following extraction was determined gravimetrically and the UV/Vis spectrum was recorded from 190 to 820 nm on a 1 mm thick flat. The data is listed in Table 1.

Example 3

Preparation of Ophthalmic Lens Material initiated with UV absorbing initiator prepared in Example 1.

A scintillation vial was charged with 3.3502 g (19.012 mmol) of 2-phenylethyl acrylate (PEA), 1.5516 g (8.156 mmol) of 2-phenylethyl methacrylate (PEMA), and 0.0567 g (0.286 mmol) of 1,4-butanediol diacrylate (BDDA). The monomer mixture was purged with N$_2$ and 0.0761 g (0.101 mmol) of the UV absorbing initiator prepared in Example 1 was added and allowed to dissolve. The initiated formulation was filtered through a 0.2 micron PTFE filter and dispensed into polypropylene molds. The molds were placed in an oven for 1 hr at 70° C. then 2 hrs at 110° C. The product polymer was extracted in acetone at room temperature for 16 hrs. The polymer was allowed to air dry for 1.5 hr, then placed in a 60° C. vacuum oven for 3 hrs. The weight loss following extraction was determined gravimetrically and the UV/Vis spectrum was recorded from 190 to 820 nm on a 1 mm thick flat. The data is listed in Table 1.

Example 4

Preparation of Ophthalmic Lens Material initiated with 2,2'-azobisisobutyronitrile (AIBN)

A scintillation vial was charged with 3.3580 g (19.057 mmol) of 2-phenylethyl acrylate (PEA), 1.5629 g (8.215 mmol) of 2-phenylethyl methacrylate (PEMA), and 0.0589 g (0.297 mmol) of 1,4-butanediol diacrylate (BDDA). The monomer mixture was purged with N₂ and 0.0502 g (0.306 mmol) of 2,2'-azobisisobutyronitrile (AIBN) was added and allowed to dissolve. The initiated formulation was filtered through a 0.2 micron PTFE filter and dispensed into polypropylene molds. The molds were placed in an oven for 1 hr at 70° C. then 2 hrs at 110° C. The product polymer was extracted in acetone at room temperature for 16 hrs. The polymer was allowed to air dry for 1.5 hr, then placed in a 60° C. vacuum oven for 3 hrs. The weight loss following extraction was determined gravimetrically and the UV/Vis spectrum was recorded from 190 to 820 nm on 1 mm thick flat. The data is listed in Table 1.

TABLE 1

Weight % acetone extractables and UV cut-off of ophthalmic lens materials.

| Example | % extractables | 10% T (nm) | 1% T (nm) |
|---------|----------------|------------|-----------|
| 2 | 3.86 ± 0.18 | 381 | 377 |
| 3 | 4.82 ± 0.25 | 377 | 371 |
| 4 | 0.63 ± 0.23 | 294 | 279 |

This invention has been described by reference to certain preferred embodiments; however, it should be understood that it may be embodied in other specific forms or variations thereof without departing from its special or essential characteristics. The embodiments described above are therefore considered to be illustrative in all respects and not restrictive, the scope of the invention being indicated by the appended claims rather than by the foregoing description.

I claim:

1. A dual function UV absorber of the formula:

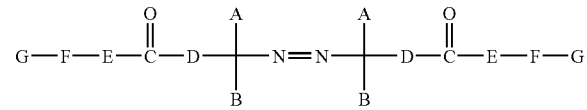

where:

A is —CH₃ or —CH₂CH₃.

B is —CN, —CO₂H, —COH, —COCH₃, —CO₂CH₃, —SO₃H, —CF₃, or —NO₂ when D is (CH₂)$_n$, and —CH₃ or —CH₂CH₃ when D is nothing.

D is nothing or (CH₂)$_n$, n=1–10

E is O or NH, NCH₃, or NCH₂CH₃

F is nothing, (CH₂)$_x$ or (CH₂CH₂O)$_x$CH₂CH₂ where x=1–10.

G is —R, —OR, —NHR, —NRR', —CO₂R, or —COR, where R=hydroxyphenylbenzotriazole, and R'=—CH₃ or —CH₂CH₃.

2. An ophthalmic lens material comprising a dual function UV absorber of claim 1.

3. The ophthalmic lens material of claim 2 wherein the dual function UV absorber is present in the ophthalmic lens material in an amount of 1–5% (w/w).

4. The dual function UV absorber of claim 1 wherein R=2-N-(2-hydroxyphenyl)benzotriazole.

* * * * *